(12) United States Patent
Ni et al.

(10) Patent No.: US 11,441,133 B2
(45) Date of Patent: Sep. 13, 2022

(54) ACINETOBACTER AND USE THEREOF IN PRODUCTION OF CHIRAL 3-CYCLOHEXENE-1-CARBOXYLIC ACID

(71) Applicant: JIANGNAN UNIVERSITY, Wuxi (CN)

(72) Inventors: Ye Ni, Wuxi (CN); Zhe Dou, Wuxi (CN); Guochao Xu, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 0 days.

(21) Appl. No.: 15/734,969

(22) PCT Filed: Nov. 22, 2019

(86) PCT No.: PCT/CN2019/120238
§ 371 (c)(1),
(2) Date: Dec. 3, 2020

(87) PCT Pub. No.: WO2020/224232
PCT Pub. Date: Nov. 12, 2020

(65) Prior Publication Data
US 2021/0230566 A1    Jul. 29, 2021

(30) Foreign Application Priority Data
May 8, 2019   (CN) .......................... 201910380623.9

(51) Int. Cl.
*C12P 7/40*   (2006.01)
*C12N 9/18*   (2006.01)

(52) U.S. Cl.
CPC ................. *C12N 9/18* (2013.01); *C12P 7/40* (2013.01); *C12Y 114/19001* (2013.01)

(58) Field of Classification Search
CPC ... C12N 15/52; C12N 9/18; C12P 7/04; C12P 7/40; C12Y 114/19001; C12Y 102/0105
USPC .......... 435/147, 196, 197, 252.3, 320.1, 136
See application file for complete search history.

(56) References Cited

U.S. PATENT DOCUMENTS

2004/0138429 A1   7/2004   Patil et al.
2009/0238811 A1   9/2009   Mcdaniel

FOREIGN PATENT DOCUMENTS

| CN | 1408848 A | 4/2003 |
| CN | 104845922 A | 8/2015 |
| CN | 106119303 A | 11/2016 |
| CN | 110272839 A | 9/2019 |

OTHER PUBLICATIONS

Kim et al., Gene Cloning, Sequencing, and Expression of an Esterase from Acinetobacter Iwoffii I6C-1, Current Microbiology vol. 46 (2003), pp. 291-295 (Dec. 31, 2003).
Ma et al., Increased Catalyst Productivity in alpha-Hydroxy Acids Resolution by Esterase Mutation and Substrate Modification, ACS Catalysis, vol. 4, pp. 1026-1031 (Feb. 17, 2014).

*Primary Examiner* — Robert B Mondesi
*Assistant Examiner* — Mohammad Y Meah
(74) *Attorney, Agent, or Firm* — SZDC Law P.C.

(57) ABSTRACT

The invention discloses a strain of *Acinetobacter* and use thereof in the production of chiral 3-cyclohexene-1-carboxylic acid. Its taxonomic name is *Acinetobacter* sp., which is deposited on Jan. 21, 2019 at the China General Microbiological Culture Collection Center, under accession number CGMCC No. 17220. Using the *Acinetobacter* strain of the invention to produce chiral methyl 3-cyclohexene-1-carboxylate, the resulting methyl (S)-3-cyclohexene-1-carboxylate has an optical purity of 99% or more, and the catalyst has good stability, mild reaction condition and can withstand high concentrations of substrate and product. Using the resolution process of the invention, (S)-3-cyclohexene-1-carboxylic acid with high optical purity and high concentration can be simply and efficiently obtained, and the process is energy-saving and environmentally friendly, and the high-concentration of product is beneficial to downstream product recovery process. The invention provides an efficient method for production of (S)-3-cyclohexene-1-carboxylic acid, and has a good industrial application prospect.

6 Claims, No Drawings ically, (R)-3-cyclo-
ACINETOBACTER AND USE THEREOF IN PRODUCTION OF CHIRAL 3-CYCLOHEXENE-1-CARBOXYLIC ACID This application is the National Stage Application of PCT/CN2019/120238, filed on Nov. 12, 2019, which claims priority to Chinese Patent Application No. 201910380623.9, filed on May 8, 2019, which is incorporated by reference for all purposes as if fully set forth herein.

FIELD OF THE INVENTION

The present invention relates to the field of microbial technology, and particularly to a strain of *Acinetobacter* and use thereof in the production of chiral 3-cyclohexene-1-carboxylic acid.

BACKGROUND OF THE INVENTION

As a chiral compound, 3-cyclohexene-1-carboxylic acid is an important chemical reagent and organic intermediate, and is widely used in many fields such as medicine and chemical industry. (S)-3-cyclohexene-1-carboxylic acid is an important starting material of an intermediate 3,4-diaminocyclohexane carboxylic acid derivatives for an inhibitor of blood coagulation factor Xa, Edoxaban. (R)-3-cyclohexene-1-carboxylic acid can also be used to synthesize a variety of drug intermediates, such as an intermediate of an anti-tumor drug (+)-Phyllanthocin, C24-C34 fragments of FK 506 (Prograf), and a starting material for oseltamivir phosphate (Tamiflu).

At present, there are only a few literature reports on the resolution preparation of chiral 3-cyclohexene-1-carboxylic acid. For example, Cihangir Tanyeli et al. (Tetrahedron Asymmetry, 2004, 15, 2057-2060) described the preparation of chiral 3-cyclohexene-1-carboxylic acid by using commercial pig liver esterase (PLE), horse liver esterase (HLE) and porcine pancreatic lipase (PPL) to hydrolyze methyl (R,S)-3-cyclohexene-1-carboxylate, where the PLE catalyzed the reaction to yield an (S)-configuration carboxylic acid with a conversion rate of 49%, e.e.>99%, and HLE catalyzed the hydrolysis of the substrate to generate an (S)-configuration carboxylic acid with a conversion rate of up to 48%, e.e. 97%, and on the contrary, PPL generates a (R)-configuration carboxylic acid with an e.e. of 91% and a conversion rate of 49%. Xu Chunxiu et al. (Modern Pharmacy and Clinic, 2013, 28(2):126-128) reported in 2013 that using chiral phenethylamine as a chiral resolving agent by means of chemical resolution, diastereoisomers of (R,S)-3-cyclohexene-1-carboxylic acid were formed in acetone, and was resolved with their solubility difference into (R)-(+)-3-cyclohexene-1-carboxylic acid (yield 28.3%) and (S)-(−)-3-cyclohexene-1-carboxylic acid (yield 28.7%), with an optical purity of greater than 99% for both. Sheng Wu et al. (Applied and Environmental Microbiology, 2016, AEM.01817-16) used Mhg esterase to hydrolyze methyl 3-cyclohexene-1-carboxylate to yield chiral 3-cyclohexene-1-carboxylic acid, with a conversion rate of the substrate of 53% and an e.e. value of 25%. Wang Zhao et al. described in a patent a process of preparing chiral 3-cyclohexene-1-carboxylic acid by resolution with a commercial protease, with a yield of 32.8% and an e.e. value of 99.5%.

However, these studies have certain limitations, for example: commercial enzymes are expensive, the substrate concentration of the catalyzed hydrolysis reaction is low, the catalysis process using microbial enzymes suffers from low stereoselectivity, and chiral resolution reagents in chemical methods are very expensive. Therefore, there is still a lack of microbial enzymes that can catalyze methyl 3-cyclohexene-1-carboxylate with high stereoselectivity to produce chiral 3-cyclohexene-1-carboxylic acid.

SUMMARY OF THE INVENTION

In order to solve the above technical problems, the present invention provides a strain of *Acinetobacter* which is capable of producing an esterase that can enantioselectively catalyzes the hydrolysis of a high-concentration substrate, and provides a method of producing a high-concentration product (S)-3-cyclohexene-1-carboxylic acid by using said strain or the crude enzyme produced therefrom to catalyze the enantioselective hydrolysis of methyl (R,S)-3-cyclohexene-1-carboxylate.

The first object of the present invention is to provide a strain of *Acinetobacter*, wherein its taxonomic name is *Acinetobacter*, deposited on Jan. 21, 2019 at the China General Microbiological Culture Collection Center, located at 3, Courtyard No. 1, Beichen West Road, Chaoyang District, Beijing, under accession number CGMCC No. 17220.

The second object of the present invention is to provide use of the *Acinetobacter* strain described above in the production of (S)-3-cyclohexene-1-carboxylic acid.

Preferably, an esterase produced by fermentation of the *Acinetobacter* strain is used as a catalyst to catalyze the production of (S)-3-cyclohexene-1-carboxylic acid from methyl (R,S)-3-cyclohexene-1-carboxylate.

Preferably, the catalysis specifically includes catalyzing the enantioselective hydrolysis of methyl (R,S)-3-cyclohexene-1-carboxylate in a buffer solution containing a cosolvent, and then collecting methyl (S)-3-cyclohexene-1-carboxylate is from the resulting mixture after the hydrolysis reaction, and performing hydrolysis by heating under an alkaline condition to yield (S)-3-cyclohexene-1-carboxylic acid.

Preferably, the cosolvent is an organic solvent mutually soluble with water.

Preferably, the added amount of the cosolvent is 5-35% of the total volume of the reaction solution.

Preferably, the buffer solution is citrate buffer, phosphate buffer or glycine-NaOH buffer, and has a pH of 5.0-9.5.

Preferably, the alkaline condition is a 0.5-1.5 M NaOH solution.

The third object of the present invention is to provide an esterase produced by fermentation of the *Acinetobacter*.

The fourth object of the present invention is to provide a microbial agent comprising the *Acinetobacter*.

As compared with the prior art, the invention has the following beneficial effects:

It has significant advantages to use the *Acinetobacter* of the present invention to produce chiral methyl 3-cyclohexene-1-carboxylate. The resulting product methyl (S)-3-cyclohexene-1-carboxylate has an optical purity of 99% or more, and the catalyst has good stability and can withstand a high concentration of a substrate and a product, and the reaction condition is mild. Using the resolution process of the present invention, (S)-3-cyclohexene-1-carboxylic acid with high optical purity and high concentration can be simply and efficiently obtained, and said process is energy-saving and environmentally friendly, and the high-concentration product is beneficial to product recovery. As a result, the present invention provides an efficient method for production of (S)-3-cyclohexene-1-carboxylic acid, which has a good industrial application prospect.

Deposit of Biological Materials

A strain of acinetobacter, *Acinetobacter* sp., was deposited on Jan. 21, 2019 at the China General Microbiological Culture Collection Center, located at 3, Courtyard No. 1, Beichen West Road, Chaoyang District, Beijing, under accession number CGMCC No. 17220. During the pendency of this application, access to the present invention will be afforded to the Commissioner upon request; all restrictions upon availability to the public will be irrevocably removed upon granting of the patent; the deposits will be maintained in a public depository for a period of 30 years or 5 years after last request or for the effective life of the patent, whichever is longer; the deposits were viable at the time of deposit; and the deposits will be replaced if they should ever become non-viable.

DETAILED DESCRIPTION OF THE INVENTION

The present invention will be further described below in conjunction with specific examples, so that those skilled in the art can better understand and implement the present invention, but the examples described here are not intended to limit the present invention.

The culture media used in the present invention are:

Enrichment medium (g/L): methyl cyclohexene carboxylate 1.5, $(NH_4)_2SO_4$ 2, $KH_2PO_4$, $MgSO_4$ 0.5, NaCl 1, DMSO 5% (v/v), pH 7.0, high temperature sterilization at 121° C. for 20 min. A small amount of soil sample was taken and suspended in a test tube containing the enrichment medium, and cultured at 30° C. and 180 rpm for 48 h. An appropriate amount of the culture solution was withdrawn and transferred to a test tube containing the second round of the enrichment medium, and further cultured under the same conditions for 48 h.

Plate separation medium (g/L): tributyrin 10, Tween-80 10, peptone 16, yeast extract 10, NaCl 5, agar 15, $KH_2PO_4$ 0.5, $MgSO_4$ 0.2, pH 7.0, high temperature sterilization at 121° C. for 20 min. The culture solution was gradient-diluted and spread on the plate medium, and a single colony with a transparent circle was a target colony.

Fermentation medium (g/L): glycerol 15, peptone 5, yeast extract 5, NaCl 1, $KH_2PO_4$ 0.5, pH 7.0, high temperature sterilization at 121° C. for 20 min. Sterilization was followed by cooling and inoculation with an inoculation volume of 5% (v/v). Fermentation was carried out at 30° C. and 180 rpm. The wet cell weight could reach 20 g/L after 12 h of culture. The specific activity (U) of the enzyme was defined as the amount of cells required to catalyze 1 μmol methyl (R,S)-3-cyclohexene-1-carboxylate per min. The measured enzyme production of JNU9335 could reach 180 U/L and the specific activity was 9 U/g wet cells.

Reaction conditions for enantioselectively catalytic hydrolysis: cell concentration 20-200 g/L, substrate concentration 50-500 mM, reaction temperature 10-60° C., pH 5-9.5, reaction time 0.5-36 h.

The enantiomeric excess (e.e.) and conversion rate of the substrate were analyzed by gas chromatography under the following analysis conditions: B-DM chiral column (30 m×0.25 mm×0.25 μm); nitrogen as carrier gas; injection port temperature 280° C.; air flow rate 300 mL/min, make-up gas flow rate 25 mL/min; split ratio 50:1; injection volume 1.0 μL. Column temperature program: 100° C. for 2 min, ramp at 2° C./min to 150° C. for 2 min. FID detector temperature: 280° C.

Example 1: Screening of *Acinetobacter*

Screening was carried out from more than 300 soils in Jiangsu, Shaanxi, Shandong, Henan, Jiangxi and other regions, and the specific screening steps were as follows.

Soil samples were collected from different environments, methyl cyclohexene carboxylate was used as the only carbon source for three rounds of enrichment culture, and esterase producing bacteria were screened. Through repeated screening, 7 strains with high enantioselective catalytic activity were isolated, and the 7 candidate strains were further analyzed and screened for the best performance.

Performance of 7 candidate strains in enantioselective hydrolysis of methyl (R,S)-3-cyclohexene-1-carboxylate:

1.0 g of wet cells of each strain were suspended in 10 mL of phosphate buffer solution (100 mM, pH 7.0). The concentration of methyl (R,S)-3-cyclohexene-1-carboxylate was 50 mM and the addition amount of cosolvent DMSO was 5%. The reaction mixture was reacted on a constant temperature shaker at 30° C. and 180 rpm. Samples were taken at the time shown in Table 1. The product and the substrate were extracted with ethyl acetate, and dried with anhydrous $Na_2SO_4$, and then subjected to chiral gas chromatography to analyze the conversion rate and enantiomeric excess value of the substrate ($e.e._s$). The catalytic performance of each strain is shown in Table 1.

TABLE 1

Comparison of catalytic performance of candidate strains

| Microbial strain | Reaction time (h) | e.e.s (%) | Conversion rate (%) |
| --- | --- | --- | --- |
| JNU9335 | 12 | 99.5 | 46 |
| JNU9308 | 12 | 96.9 | 41 |
| JNU9324 | 12 | 98.0 | 41 |
| JNU9210 | 12 | 91.9 | 39 |
| JNU9124 | 12 | 95.5 | 36 |
| JNU9105 | 12 | 99.1 | 28 |
| JNU9008 | 12 | 99.9 | 25 |

Table 1 shows that these 7 strains screened from the soil all have high enantioselective catalytic activity, among which JNU9335 has the fastest reaction speed and the highest conversion rate.

Tolerance of 7 candidate strains to different concentrations of methyl (R,S)-3-cyclohexene-1-carboxylate:

1 g of wet cells of each strain were suspended in 10 mL of phosphate buffer solution (100 mM, pH 7.0). Methyl (R,S)-3-cyclohexene-1-carboxylate at different concentrations were added, and the reaction mixture was reacted on a constant temperature shaker at 30° C. and 180 rpm. Samples were taken after the reaction, the product and the substrate were extracted with ethyl acetate, dried over anhydrous $Na_2SO_4$, and then subjected to chiral gas chromatography to analyze the conversion rate of the substrate. The tolerance of each strain to different concentrations of the substrate is shown in Table 2.

TABLE 2

Comparison of the tolerance of candidate strains to different concentrations of the substrate

| | Methyl (R,S)-3-cyclohexene-1-carboxylate concentration (mM) | | |
| --- | --- | --- | --- |
| Microbial strain | 100 mM | 200 mM | 500 mM |
| JNU9335 | 46 | 90 | 197 |
| JNU9308 | 42 | 48 | 60 |

TABLE 2-continued

Comparison of the tolerance of candidate strains
to different concentrations of the substrate

| Microbial strain | Methyl (R,S)-3-cyclohexene-1-carboxylate concentration (mM) | | |
|---|---|---|---|
| | 100 mM | 200 mM | 500 mM |
| JNU9324 | 42 | 15 | 12 |
| JNU9210 | 34 | 30 | 30 |
| JNU9124 | 32 | 12 | 20 |
| JNU9105 | 20 | 40 | 40 |
| JNU9008 | 20 | 40 | 39 |

Table 2 shows that as the substrate concentration increases, the activity of most strains is inhibited by the higher substrate concentration, and the increase in hydrolysate is very small. Only strain JNU9335 can still maintain a higher conversion rate and yield a higher concentration of the product at a higher substrate concentration (500 mM), indicating that the strain has excellent substrate and product tolerance. Thus, this strain was selected as the optimal strain for future work.

Through the above screening, an esterase-producing bacterium JNU9335 that is stable in enzyme production with high activity and high selectivity was obtained. The strain was deposited on Jan. 21, 2019 at the China General Microbial Culture Collection and Management Center under the accession number CGMCC No. 17220.

Example 2: Morphological and Physiological Identification of *Acinetobacter* sp. JNU9335

The strain JNU9335 has the following microbiological characteristics:

1. Shape and size

Rod-shaped, uniformly stained, 0.5-0.9×1.5-3 μm, non-spore-forming, no flagella, Gram-staining negative.

2. Suitable growth environment

The suitable growth temperature is 20-35° C., and it can survive in pH 5-9 environment.

3. Characteristics of plate culture colony

A small colony can be formed after culture on a plate at 30° C. for 24 h, and a viscous, moist white colony with a smooth edge and a prominent middle is formed at 36 h. A transparent circle is formed on the tributyrin plate over time.

Example 3: Molecular Biological Identification of *Acinetobacter* sp. JNU9335

The chromosomal DNA of strain JNU9335 was extracted, and the 16S ribosomal DNA (16S rDNA) was amplified enzymatically with primers (27F: 5'-AGAGTTTGATCCTGGCTCAG-3'; 1492R: 5'-TACCTTGTTACGACTT-3'). The PCR program of a thermal cycler was: denaturation at 95° C. for 5 min, at 95° C. for 40 s, 30 cycles of at 55° C. for 1 min and at 72° C. for 2 min, and the last step at 72° C. for 10 min. Analysis of 16S rDNA sequencing results identified it as *Acinetobacter* sp.

Example 4: Fermentation Culture of *Acinetobacter* sp. JNU9335

Fermentation medium (g/L): glycerol 15, peptone 5, yeast extract 5, NaCl 1, $KH_2PO_4$ 0.5, pH 7.0. High temperature sterilization at 121° C. for 20 min. Sterilization was followed by cooling and inoculation with an inoculation volume of 5% (v/v). Fermentation was carried out at 30° C. and 180 rpm for 12 h. The cells were collected at 8000 rpm for 10 min with the upper medium being discarded, washed once with normal saline, and dried in a vacuum freeze dryer (SCIENTZ-10N) for 24 h. The enzyme powder was collected for storage at −20° C. The activity (U) of the enzyme was defined as the amount of cells required to catalyze 1 μmol methyl (R,S)-3-cyclohexene-1-carboxylate per min. The specific activity of the enzyme powder was measured to be 96 U/g.

Example 5: Effect of Temperature on the Enzymatic Hydrolysis of Methyl Cyclohexene Carboxylate 70 mg methyl (R,S)-3-cyclohexene-1-carboxylate, 0.5 mL dimethyl sulfoxide, 25 mg lyophilized crude enzyme powder were added to 10 mL phosphate buffer (100 mM, pH 7.0), uniformly mixed, and reacted on a constant temperature shaker at 180 rpm for 6 h at 20, 30, 40 and 50° C., respectively. Samples were taken after the reaction, and the product and the substrate were extracted with ethyl acetate, dried over anhydrous $Na_2SO_4$, and then subjected to chiral gas chromatography to analyze the conversion rate and enantiomeric excess value of the substrate ($e.e._s$). As shown in Table 3, when the temperature is 20-40° C., the esterase has a high conversion rate and stable $e.e._s$, indicating that the esterase is relatively stable without great activity loss within this temperature range. When the temperature exceeds 50° C., the conversion capacity of the esterase is greatly reduced. This may be due to the changes in spatial configuration of the esterase caused by high temperature, which leads to the decrease in enzyme activity.

TABLE 3

Effect of temperature on the enzymatic hydrolysis of methyl (R,S)-3-cyclohexene-1-carboxylate catalyzed by acinetobacter esterase

| Temperature (° C.) | $e.e._s$ (%) | Conversion rate (%) |
|---|---|---|
| 20 | 99.5 | 32 |
| 30 | 99.4 | 46 |
| 40 | 99.3 | 40 |
| 50 | 99.5 | 25 |

Example 6: Enzymatic Hydrolysis of Methyl (R,S)-3-Cyclohexene-1-Carboxylate at Different Concentrations by *Acinetobacter* Esterase Methyl (R,S)-3-cyclohexene-1-carboxylate at 100, 200 and 500 mM, respectively and 0.5 mL dimethyl sulfoxide were added to 10 mL phosphate buffer (100 mM, pH 7.0), and respective amounts of the enzyme were added respectively. The reaction mixture was put on a constant temperature shaker to react at 30° C. and 180 rpm. Samples were taken after the reaction, and the product and the substrate were extracted with ethyl acetate, dried over anhydrous $Na_2SO_4$, and then subjected to chiral gas chromatography to analyze the conversion rate and enantiomeric excess value of the substrate ($e.e._s$). The results are shown in Table 4.

TABLE 4

Enzymatic hydrolysis of methyl (R,S)3-cyclohexene-1-carboxylate at different concentrations by acinetobacter esterase

| Substrate concentration (mM) | Reaction time (h) | Product concentration (mM) | e.e., (%) |
|---|---|---|---|
| 100 | 3 | 48 | 99.5 |
| 200 | 6 | 94 | 99.4 |
| 500 | 12 | 215 | 99.1 |

Table 4 shows that when the esterase catalyzes different concentrations of methyl (R,S)-3-cyclohexene-1-carboxylate, the product concentration increases as the substrate concentration increases and is up to 215 mM, and the product still has a high optical purity, indicating that higher concentrations of the substrates and the product do not have a significant impact on the activity of the *Acinetobacter* esterase, which can tolerate high concentrations of the substrates and the product. This is an example with the highest concentration of the product among the biocatalytic methods for the production of chiral cyclohexene carboxylic acid that have been reported so far, and it is also the only report on microbial enzymatic conversion. The method of the present invention has very broad practical industrial application prospects.

Example 7: Gram Scale Preparation of (S)-Cyclohexene-1-Carboxylic Acid 3.50 g methyl (R,S)-3-cyclohexene-1-carboxylate was uniformly mixed with 2.5 mL dimethyl sulfoxide and 47.5 mL phosphate buffer (200 mM, pH 7.0), and 1 g enzyme powder was added thereto. The reaction was carried out in a 250 mL round-bottomed flask at a constant temperature of 30° C., with mechanical stirring at 400 rpm. The conversion rate of the substrate and the enantiomeric excess of the product were monitored by means of chiral gas chromatography. After 12 h, the reaction was ended. After filtering to remove the enzyme, the pH was adjusted to 9, and ethyl acetate was added for extraction 3 times. The organic phases were combined and rotary evaporated until no liquid flowed out to obtain methyl (S)-3-cyclohexene-1-carboxylate. Then methyl (S)-3-cyclohexene-1-carboxylate was added to a 1 M NaOH aqueous solution, and heated to reflux at 50° C. with stirring for 6 h. A 1 M HCl aqueous solution was then added to adjust the pH to 5. An equal volume of ethyl acetate was added for extraction 3 times. The organic layers were combined, dried over anhydrous $Na_2SO_4$, filtered, and rotary evaporated to obtain (S)-3-cyclohexene-1-carboxylic acid. The resulting product was a liquid with a special odor. The total yield after separation was 40%, with an optical purity of 99% e.e.

The examples described above are only preferred examples for fully explaining the present invention and the protection scope of the present invention is not limited thereto. Equivalent substitutions or changes made by those skilled in the art on the basis of the present invention are all within the protection scope of the present invention. The protection scope of the present invention is defined by the claims.

What is claimed is:

1. A method for preparing (S)-3-cyclohexene-1-carboxylic acid, comprising:
    isolating a strain of *Acinetobacter*, wherein a taxonomic name thereof is *Acinetobacter* sp., deposited on Jan. 21, 2019 at the China General Microbiological Culture Collection Center, located at No. 1, Beichen West Road, Chaoyang District, Beijing, under accession number CGMCC No. 17220;
    producing an esterase by fermenting of the strain of *Acinetobacter* sp.; and
    using the esterase as a catalyst to catalyze a reaction for producing the (S)-3-cyclohexene-1-carboxylic acid from a methyl (R,S)-3-cyclohexene-1-carboxylate.

2. The method according to claim 1, wherein the catalysis specifically comprising catalyzing the enantioselective hydrolysis of the methyl (R,S)-3-cyclohexene-1-carboxylate in a buffer solution containing a cosolvent, and then collecting a methyl (S)-3- cyclohexene-1-carboxylate from the resulting mixture after hydrolysis, and performing hydrolysis of the said methyl (S)-3-cyclohexene-1-carboxylate by heating under an alkaline condition to obtain the (S)-3-cyclohexene-1-carboxylic acid.

3. The method according to claim 2, wherein the cosolvent is an organic solvent mutually soluble with water.

4. The method according to claim 2, wherein amount of the cosolvent added is 5-35% of the total volume of the solution.

5. The method according to claim 2, wherein the buffer solution is citrate buffer, phosphate buffer or glycine-NaOH buffer, and has a pH of 5.0-9.5.

6. The method according to claim 2, wherein the alkaline condition is a 0.5-1.5 M NaOH solution.

* * * * *